United States Patent

Groux et al.

Patent Number: 5,336,247
Date of Patent: Aug. 9, 1994

[54] HAIR REGROWTH METHOD AND APPARATUS

[75] Inventors: Paul D. Groux, Clovis; Marvin A. Burgess, La Mesa, both of Calif.

[73] Assignee: 314613 B.C. Ltd., Vancouver, Canada

[21] Appl. No.: 36,447

[22] Filed: Mar. 24, 1993

Related U.S. Application Data

[63] Continuation of Ser. No. 604,744, Oct. 26, 1990, Pat. No. 5,251,623.

[51] Int. Cl.⁵ ............................................. A61N 1/36
[52] U.S. Cl. ................................... 607/72; 607/50; 607/139
[58] Field of Search .................. 128/421, 422, 419 R, 128/420 R, 423 R, 791, 802; 607/2, 50, 72, 139, 153

[56] References Cited

U.S. PATENT DOCUMENTS

| | | |
|---|---|---|
| 629,340 | 7/1899 | Cook . |
| 735,581 | 8/1903 | Pollacsek et al. . |
| 740,385 | 10/1903 | Bassell . |
| 861,349 | 7/1907 | Beaubien . |
| 1,099,062 | 6/1914 | Laposkey ........................... 128/791 |
| 1,706,583 | 3/1929 | Meyer . |
| 3,387,147 | 6/1968 | Brown ................................ 128/791 |
| 3,589,370 | 6/1971 | McDonald . |
| 3,872,859 | 3/1975 | Pitzen et al. . |
| 3,946,745 | 3/1976 | Hsiang-Lai et al. . |
| 4,019,510 | 4/1977 | Ellis ................................... 128/421 |
| 4,406,658 | 9/1983 | Lattin et al. ....................... 128/419 R |
| 4,709,702 | 12/1987 | Sherwin ............................ 128/791 |
| 4,765,316 | 8/1988 | Marshall . |

FOREIGN PATENT DOCUMENTS

2952850A1 4/1981 Fed. Rep. of Germany .
1350890 12/1962 France .

OTHER PUBLICATIONS

"An Examination of Evidence and Information Respecting Hair Regrowth Through the Electrical Stimulation of the Scalp in Cases of Male Pattern Baldness", Peter W. Bell, Appendix 1, pp. 1-11, Current Technology Corporation Prospectus, 30 Jun., 1988.

*Primary Examiner*—William E. Kamm
*Attorney, Agent, or Firm*—Oyen Wiggs Green & Mutala

[57] ABSTRACT

Hair regrowth is promoted by positioning one or more electrodes closely proximate a subject's scalp. A low voltage positive or negative polarity signal having a selected frequency of either 7.86 or 15.72 hertz is applied to the electrode(s) for about twelve minutes. The subject undergoes a hair regrowth treatment cycle spanning a period of about thirty-two weeks during which one or two of the treatments aforesaid are applied per week.

6 Claims, 2 Drawing Sheets

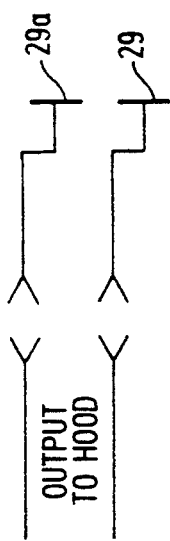
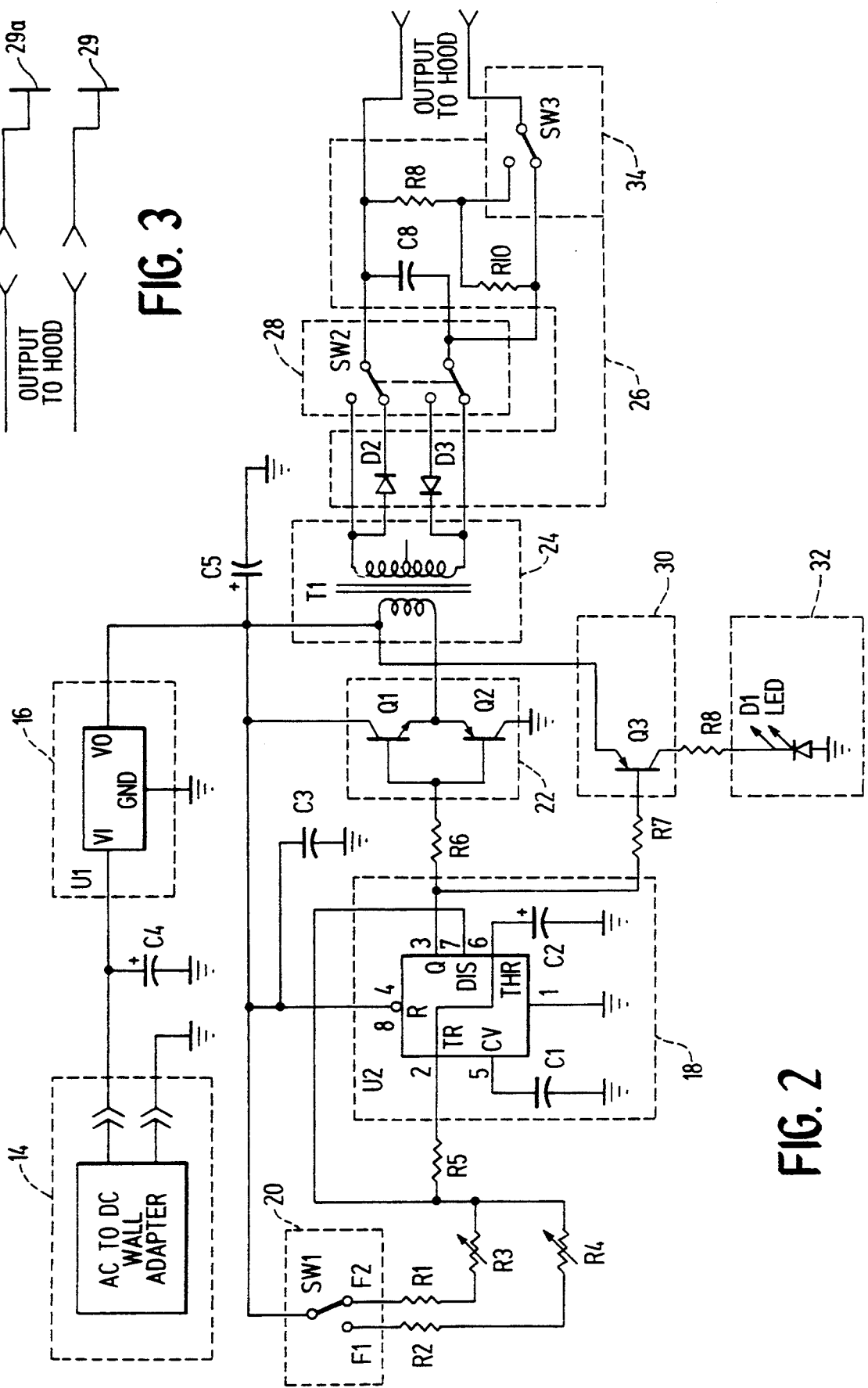
FIG. 3
FIG. 2

HAIR REGROWTH METHOD AND APPARATUS

This is a continuation of application Ser. No. 07/604,744 filed on Oct. 26, 1990, now U.S. Pat. No. 5,251,623.

FIELD OF THE INVENTION

This application pertains to a method and apparatus for promoting hair regrowth in humans.

BACKGROUND OF THE INVENTION

Many individuals are troubled by premature baldness, receding hairlines, or other conditions in which hair is lost from the head. Over the years, a variety of chemicals have been marketed as hair regrowth aids but with mixed, generally disappointing results. Many individuals have invested considerable sums in artificial hair pieces. Some individuals have even undergone surgical hair implantation procedures requiring the exercise of highly skilled medical expertise which is generally unavailable to a wide cross-section of potential beneficiaries. It will thus be appreciated that there is a need for a reasonably inexpensive hair regrowth process capable of being administered by relatively unskilled personnel and capable of promoting hair regrowth in the widest possible population cross-section.

The prior art discloses that a variety of electrical stimulii have been employed in an effort to promote hair growth. For example, U.S. Pat. No. 861,349 issued July 30, 1907 for an invention of R. E. Beaubien entitled "Apparatus for Treating the Scalp" discloses an "apparatus for promoting the growth of hair upon the human head". The apparatus appears to rely upon a combination of pneumatic, vacuum and electrical effects, in combination with the application of medicated lotions and massage to the scalp. According to Beaubien, any desirable form of electrical battery or current may be used. The present applicant however believes that this is not the case and that in order to satisfactorily promote hair regrowth, specific electrical signals must be employed.

U.S. Pat. No. 735,581 issued August 4, 1903 for an invention of Pollacsek, et al. entitled "Therapeutical Apparatus" discloses a device "by means of which vibrations of diseased parts of the body can be produced". Pollacsek, et al. indicate that the device may be shaped as a cap to be placed on the head and that the cap may be introduced into a magnetic field produced by an electric current passing through the windings of an iron core. However, there is no indication of the specific nature of the electric or magnetic signals or fields employed, nor is there any suggestion that Pollacsek, et al. considered applying their device to promote hair regrowth.

U.S. Pat. No. 740,385 issued October 6, 1903 for an invention of W. B. Bassell entitled "Electrotherapeutic Appliance" provides another device "adapted to subject the wearer to the action of a current of electricity for curative purposes". Bassell explains that his invention is to be utilized for the relief and cure of nervousness, insomnia, headache, and other kindred troubles. He suggests that this may be accomplished by subjecting the head of the wearer to the action of a comparatively mild current of electricity provided by a small battery. Again however there is no suggestion that Bassell considered the use of his device to promote hair regrowth, nor are any specific electrical signals discussed.

U.S. Pat. No. 3,872,859 issued March 25, 1975 for an invention of Pitzen, et al. entitled "Method and Device for Stimulating the Organs Associated with the Human Scalp" examines the problem of promoting hair growth in some detail. Pitzen, et al. provide a method and apparatus in which a plurality of wave form generators output signals having frequencies varying from 230 hertz through 2650 hertz. The waveform generators are also pulsed at repetition rates varying from 3 times per second to 26 times per second. The signals so produced are applied to hand-held massaging electrodes which are in turn applied to the subject's scalp.

Published French patent application No. 2,484,262 of Paul Maurice Viallis provides another electrical apparatus and method for treating the human scalp to combat seborrhoea, hair loss, dandruff, etc. A conductive electrode cap is fitted over the scalp and a secondary electrode is placed in contact with another area of the body. A current of the order of 8-15 mA is applied for a period of 5 to 30 minutes depending upon the type of complaint and type of treatment prescribed. The object of Viallis' invention is apparently to ionize the scalp area so that ointments or other applied treatment compositions may penetrate the scalp with greater effectiveness.

Published West German patent application No. 3,618,933 discloses an invention of Masaki, et al. pertaining to an electrotherapeutic device for promoting eyebrow hair growth. The apparatus is shaped to fit on a patient's head. Electrodes are applied to the eyebrows. A pulse-like current preferably having a square or trapezoid waveform is applied to the electrodes, with a biphasic action, potential-like oscillation having a frequency in the 1/500 to 1/200 second range and pulsed at a frequency of 0.5 to 2 seconds is preferably applied to the electrodes.

Two published British patent application Nos. 2,160,426A and 2,160,427A of Masaki appear to correspond to the West German application aforesaid, although the British applications do not appear to restrict themselves to eyebrow hair growth.

Although not wishing to be bound by any theory, the inventors believe that dormant body hair cells (i.e. hair cells from which hair is not actively growing) may be electrically stimulated to promote active hair growth from such cells. More particularly, the inventors believe that hair regrowth can be promoted if the body's hair cells are stimulated by subjecting them to a low voltage pulse train having a frequency of about 7.86 hertz or 15.72 hertz. The higher frequency is considered appropriate for subjects who exhibit normal or hyperactive energy levels. The lower frequency is considered appropriate for individuals who exhibit hypoactive or slow metabolism energy levels.

SUMMARY OF THE INVENTION

In accordance with the preferred embodiment, the invention provides a hair regrowth process in which one or more electrodes are positioned closely proximate the subject's scalp. A low voltage electrical signal having a frequency of about 7.86 hertz or about 15.72 hertz is continuously applied to the electrodes for about twelve minutes. The polarity of the signal may be either positive or negative. A complete hair regrowth treatment cycle typically spans about thirty-two weeks, during which time the subject undergoes a sequence of twelve minute treatments as aforesaid. Throughout the treatment cycle the subject undergoes one or two twelve minute treatments per week, during which the treatment frequency, signal polarity and voltage level are preferably varied according to the following schedule:

|  | Number of Treatments | Polarity | Voltage Level |
|---|---|---|---|
| 1st week | 2 | Positive | 260 v. |
| 2nd week | 2 | Positive | 260 v. |
| 3rd week | 1 | Negative | 260 v. |
| 4th week | 1 | Negative | 260 v. |
| 5th week | 1 | Negative | 260 v. |
| 6th week | 1 | Negative | 260 v. |
| 7th week | 1 | Negative | 260 v. |
| 8th week | 1 | Negative | 260 v. |
| 9th week | 1 | Negative | 260 v. |
| 10th week | 1 | Negative | 260 v. |
| 11th week | 1 | Negative | 260 v. |
| 12th Week | 1 | Negative | 260 v. |
| 13th week | 1 | Negative | 260 v. |
| 14th week | 1 | Negative | 260 v. |
| 15th week | 1 | Negative | 260 v. |
| 16th week | 1 | Negative | 260 v. |
| 17th week | 2 | Positive | 130 v. |
| 18th week | 2 | Positive | 260 v. |
| 19th week | 1 | Negative | 130 v. |
| 20th week | 1 | Negative | 260 v. |
| 21st week | 1 | Negative | 130 v. |
| 22nd week | 1 | Negative | 260 v. |
| 23rd week | 1 | Negative | 130 v. |
| 24th week | 1 | Negative | 260 v. |
| 25th week | 1 | Negative | 130 v. |
| 26th week | 1 | Negative | 260 v. |
| 27th week | 1 | Negative | 130 v. |
| 28th week | 1 | Negative | 260 v. |
| 29th week | 1 | Negative | 130 v. |
| 30th week | 1 | Negative | 260 v. |
| 31st week | 1 | Negative | 130 v. |
| 32nd week | 1 | Negative | 260 v. |

In accordance with the preferred embodiment, the invention provides a hair regrowth apparatus comprising at least one electrode adapted to be positioned closely proximate the subject's scalp, voltage pulse generator means electrically coupled to the electrode(s) for application thereto of a low voltage pulse train, and, frequency selector means electrically coupled to the voltage pulse generator means, for varying the frequency of the pulse train. Preferably, the apparatus also includes signal polarity selector means electrically coupled between the voltage pulse generator means and the electrode(s), for varying the polarity of the pulse train. The electrodes are advantageously mounted within a hood positionable over the subject's head.

The voltage pulse generator means is preferably an astable multivibrator. The signal polarity selector means may comprise a voltage transformer, first rectifier means for blocking negative-going portions of the pulse train, second rectifier means for blocking positive-going portions of the pulse train, and, switch means for selectably coupling the first or second rectifier means between the transformer output and the electrode(s).

BRIEF DESCRIPTION OF THE DRAWINGS

FIG. 2 is an electronic circuit schematic diagram of a hair regrowth apparatus constructed in accordance with the preferred embodiment of the invention.

FIG. 3 depicts a single electrode embodiment for the hood of the apparatus of FIG. 1.

DETAILED DESCRIPTION OF THE PREFERRED EMBODIMENT

Figure 1:
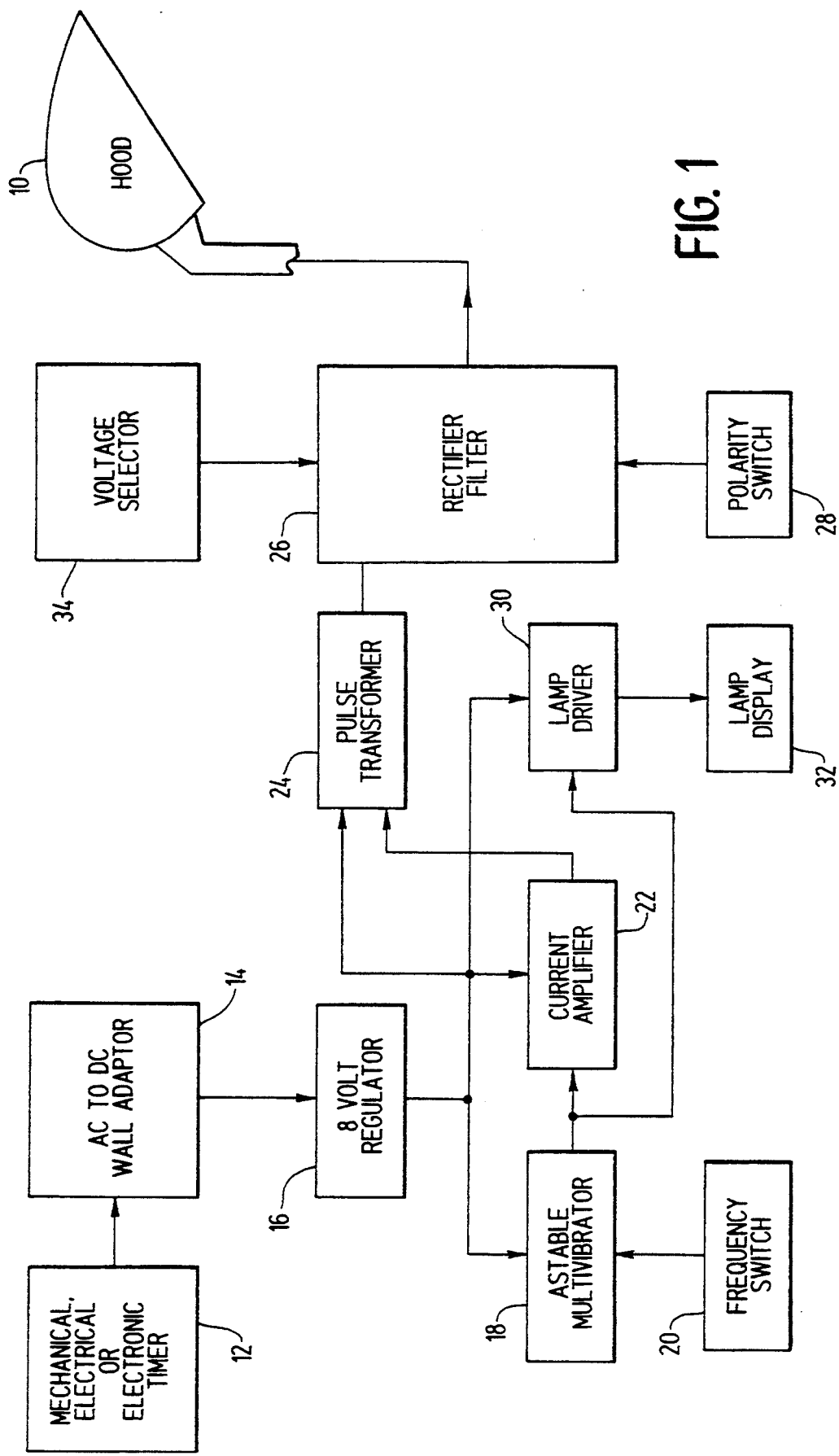
FIG. 1 is a block diagram of a hair regrowth apparatus constructed in accordance with the preferred embodiment of the invention.

As shown in FIG. 1 the interior of a conventional commercial hair dryer hood 10 is fitted with a plurality of copper electrodes so that, when the hood is positioned over a subject's head, the electrodes are positioned closely proximate to, but not touching the subject's scalp. The apparatus is turned on and off with the aid of a mechanical, electrical or electronic timer 12 operatively connected to power supply 14 which may be a conventional 110 volt A.C. to 12 volt D.C. transformer. The 12 volt D.C. signal output by power supply 14 is regulated down to 8 volts D.C. by voltage regulator 16 and the resultant 8 volt D.C. signal is then used to power the remaining electronic components.

A "voltage pulse generator means"; namely, astable multivibrator 18, is electrically coupled to the electrodes within hood 10. Astable multivibrator 18 applies a low voltage pulse train of a selected frequency to the electrodes within hood 10. Frequency selector means 20 is electrically coupled to astable multivibrator 18 to vary the frequency of the pulse train between low frequencies of either 7.86 hertz or 15.72 hertz. Lamp driver 30 provides a visual indication, via lamp display 32, of the selected frequency (i.e. lamp display 32 is switched on and off at the selected frequency).

The low voltage, low frequency pulse train output by astable multivibrator 18 is amplified by current amplifier 22 and then presented to pulse transformer 24. A "signal polarity selector means"; namely, rectifier/filter 26, is electrically coupled between astable multivibrator 18 and the electrodes within hood 10, to vary the polarity of the signals output by pulse transformer 24, according to the position manually selected via polarity switch 28.

A "voltage selector means"; namely, switch 34 is provided to vary the voltage of the pulse train applied to the electrodes within hood 10.

The apparatus of the preferred embodiment will now be described in greater detail with reference to the electronic circuit schematic diagram of FIG. 2. Power supply 14 comprises a conventional 110 volt A.C. to 12 volt, 200 milliampere D.C. "wall adaptor" voltage transformer. The 12 volt D.C. signal output by power supply 14 is electrically coupled to voltage regulator 16 which, in the preferred embodiment, is an LM7808 integrated circuit 8 volt regulator with internal current limiting, thermal shutdown capability and safe area compensation for the internal pass transistor. Capacitors C4 and C5 respectively provide low frequency filtering for the input and output of regulator 16, which produces an 8 volt D.C. output signal used to power the remaining electronic components.

Astable multivibrator 18 is a NE555 integrated circuit pulse generator. The trigger input (pin 2) of astable multivibrator 18 is connected to the threshold input (pin 6) in order to continuously retrigger the circuit for astable operation thereof. Resistors R1, R2 and R5, together with potentiometers R3 and R4 and timing capacitors C1 and C2 control the frequency of the pulse train output by astable multivibrator 18. The output frequency is selected by manual positioning of switch SW1 (reference No. 20 in FIG. 1) which is a single pole, double throw switch. When switch SW1 is in the "F1" position, astable multivibrator 18 produces a low voltage, pulse train at a first frequency. When switch SW1 is in the "F2" position astable multivibrator 18 produces a low voltage, pulse train at a second frequency. More particularly, when switch SW1 is in the "F1" position, the steady state frequency of the voltage pulse train output by astable multivibrator 18 is determined by:

$$F1 = \frac{1}{T1} = .693(R2 + R4 + R5)C2$$

Similarly, when frequency selector switch SW1 is in the "F2" position, the steady state frequency of the voltage pulse train output by astable multivibrator 18 is determined by:

$$F2 = \frac{1}{T2} = .693(R1 + R3 + R5)C2$$

The frequency selected is visually indicated by flashing light emitting diode D1, which is driven through current limiting resistor R7 and inverting amplifier transistor Q3. Resistor R8 provides current limiting for light emitting diode D1.

Capacitor C1 is used to bypass pin 5 of the astable multivibrator 18 to ground, preventing noise from altering the width of the pulses output by astable multivibrator 18. Capacitor C3 is a bypass capacitor which eliminates high frequency noise on the power line.

The low voltage, low frequency pulse train output by astable multivibrator 18 passes to a current amplifier comprising transistors Q1 and Q2, which are configured to operate in a class B switching mode to provide the higher peak currents passed through switching transformer T1. More particularly, when transformer T1 is switched on, a pulse of about 300 volts appears in the transformer primary winding. Because the transformer provides D.C. isolation, the higher voltage end of the transformer can safely be used to produce a positive or negative going pulse through the polarity selector means comprising transformer T1 together with a first rectifier means (i.e. diode D2), a second rectifier means (i.e. diode D3) and polarity switch SW2 (reference No. 28 in FIG. 1). When switch SW2 is in the "positive" polarity position, diode D2 in combination with filter capacitor C6 and discharge resistor R9 shape the pulses output by switching transformer T1, while blocking negative going portions of the pulse train. Similarly, when polarity selector switch SW2 is in the "negative" polarity position, diode D3 blocks positive-going portions of the pulse train. The voltage output across resistor R9 is coupled to the electrodes within hood 10. In case of a two electrode embodiment, the output is coupled to a pair of electrodes 29 and 29a (FIG. 3) within the hood 10. Limit resistor R10 and voltage selector switch SW3 (reference No. 34 in FIG. 1) enable the operator to select between one of two operating voltages (130 volts peak-to-peak; or, 260 volts peak-to-peak in the preferred embodiment.

The output frequency is selected by manual positioning of switch 20 which is a single pole, double throw switch. When switch SW1 is in the low frequency position, astable multivibrator 18 produces a low voltage pulse train of 7.86 hertz. When switch 20 is in the high frequency position, astable multivibrator 18 produces a low voltage 15.72 hertz pulse train.

In operation, the subject's head is positioned within hood 10, so that the hood electrodes lie closely proximate to, but do not touch the subject's scalp. Power is applied to the circuit and switches 20, 28 manually positioned to select a desired signal output frequency and polarity. Signals of the selected frequency and polarity are applied to the electrodes for about 12 minutes, following which the power is disconnected and the hood removed from the subject's head. Repetitive treatments over many weeks will be required, depending upon the individual characteristics of the particular subject.

An entire hair regrowth treatment cycle will typically span about 32 weeks, during which time the subject undergoes one or two 12 minute treatments as aforesaid per week. The following table provides the weekly treatment frequency, the signal output polarity and the voltage level preferably employed during each week of the 32 week treatment cycle:

|  | Number of Treatments | Polarity | Voltage Level |
|---|---|---|---|
| 1st week | 2 | Positive | 260 v. |
| 2nd week | 2 | Positive | 260 v. |
| 3rd week | 1 | Negative | 260 v. |
| 4th week | 1 | Negative | 260 v. |
| 5th week | 1 | Negative | 260 v. |
| 6th week | 1 | Negative | 260 v. |
| 7th week | 1 | Negative | 260 v. |
| 8th week | 1 | Negative | 260 v. |
| 9th week | 1 | Negative | 260 v. |
| 10th week | 1 | Negative | 260 v. |
| 11th week | 1 | Negative | 260 v. |
| 12th week | 1 | Negative | 260 v. |
| 13th week | 1 | Negative | 260 v. |
| 14th week | 1 | Negative | 260 v. |
| 15th week | 1 | Negative | 260 v. |
| 16th week | 1 | Negative | 260 v. |
| 17th week | 2 | Positive | 130 v. |
| 18th week | 2 | Positive | 260 v. |
| 19th week | 1 | Negative | 130 v. |
| 20th week | 1 | Negative | 260 v. |
| 21st week | 1 | Negative | 130 v. |
| 22nd week | 1 | Negative | 260 v. |
| 23rd week | 1 | Negative | 130 v. |
| 24th week | 1 | Negative | 260 v. |
| 25th week | 1 | Negative | 130 v. |
| 26th Week | 1 | Negative | 260 v. |
| 27th week | 1 | Negative | 130 v. |
| 28th week | 1 | Negative | 260 v. |
| 29th week | 1 | Negative | 130 v. |
| 30th week | 1 | Negative | 260 v. |
| 31st week | 1 | Negative | 130 v. |
| 32nd week | 1 | Negative | 260 v. |

Some subjects may respond more favorably to alternative signal polarities than those set forth above. Accordingly, based upon professional review, the treatment regimen may be varied by, for example, replacing two of the negative polarity treatments with two positive polarity treatments and then returning to negative polarity treatments as prescribed for the balance of the treatment cycle.

The following table provides electronic part specifications for the circuit components depicted in FIG. 2 and described herein.

| Reference | Description |
|---|---|
| R1-R5: C1-C2 | select |
| R6 | 22 ohms |
| R7 | 8.2K ohms |
| R8 | 100 ohms |
| R9, R10 | 560K ohms |
| C3 | .1 microfarads |
| C4 | 22 microfarads |
| C5 | 1,000 microfarads |
| C6 | .0018 microfarads |
| D1 | LED |
| D2, D3 | 1N4005 |

-continued

| Reference | Description |
| --- | --- |
| Q1 | 2N2222 |
| Q2 | 2N2906 |
| Q3 | 2N3906 |
| T1 | 42HL015 |
| U1 | LM7808 |
| U2 | NE555 |
| SW1, SW3 | single pole double throw |
| SW2 | polarity switch |

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

I claim:
1. Hair regrowth apparatus comprising:
   at least two electrodes;
   positioning means for positioning the at least two electrodes closely proximate to, but not touching, a subject's scalp;
   voltage pulse generator means electrically coupled to said at least two electrodes for application thereto of a low voltage, low frequency pulse train signal; and,
   frequency selector means electrically coupled to said voltage pulse generator means, for varying said frequency.
2. Hair regrowth apparatus as defined in claim 1, further comprising polarity switching means electrically coupled between said voltage pulse generator means and said at least two electrodes, for switching said signal polarity, and polarity selector means electrically coupled to said switching means for selectively varying said signal's polarity.
3. Hair regrowth apparatus as defined in claim 2, wherein said signal polarity selector means comprises:
   (a) a voltage transformer;
   (b) first rectifier means for blocking negative-going portions of said pulse train;
   (c) second rectifier means for blocking positive-going portions of said pulse train; and,
   (d) switch means for selectably coupling said first or second rectifier means between said transformer output and said at least two electrodes.
4. Hair regrowth apparatus as defined in claim 1, wherein said voltage pulse generator means comprises an astable multivibrator.
5. Hair regrowth apparatus as defined in claim 1, further comprising voltage selector means electrically coupled between said voltage pulse generator means and said at least two electrodes, for varying the voltage of said pulse train.
6. Hair regrowth apparatus as defined in claim 1, wherein the positioning means comprises a hood positionable over said subject's head, and wherein said at least two electrodes is mounted within said hood.

* * * * *